US012721623B2

(12) United States Patent
Cobb et al.

(10) Patent No.: US 12,721,623 B2
(45) Date of Patent: Sep. 1, 2026

(54) BONE STAPLE DELIVERY DEVICES, BONE STAPLES AND METHODS OF USE THEREOF

(71) Applicant: PRIMO MEDICAL GROUP, INC., Stoughton, MA (US)

(72) Inventors: John Cobb, Stoughton, MA (US); Richard P. Rodgers, Hudson, MA (US)

(73) Assignee: Primo Medical Group, Inc., Stoughton, MA (US)

( * ) Notice: Subject to any disclaimer, the term of this patent is extended or adjusted under 35 U.S.C. 154(b) by 0 days.

(21) Appl. No.: 18/428,491

(22) Filed: Jan. 31, 2024

(65) Prior Publication Data

US 2025/0241641 A1 Jul. 31, 2025

(51) Int. Cl.
*A61B 17/072* (2006.01)
*A61B 17/00* (2006.01)

(52) U.S. Cl.
CPC .. *A61B 17/072* (2013.01); *A61B 2017/00367* (2013.01); *A61B 2017/0046* (2013.01); *A61B 2017/07278* (2013.01)

(58) Field of Classification Search
CPC ................ A61B 17/068; A61B 17/072; A61B 2017/0367; A61B 2017/0046; A61B 2017/07278
See application file for complete search history.

(56) References Cited

U.S. PATENT DOCUMENTS

| | | | | |
|---|---|---|---|---|
| 5,053,038 | A | 10/1991 | Sheehan | |
| 10,610,218 | B2 | 4/2020 | Palmer et al. | |
| D895,113 | S | 9/2020 | Blair et al. | |
| 11,116,499 | B1 | 9/2021 | Blair et al. | |
| 11,284,887 | B2 | 3/2022 | Hartdegen et al. | |
| 11,690,616 | B2 * | 7/2023 | Fein | A61B 17/0682 227/175.1 |
| 2010/0133316 | A1 | 6/2010 | Lizee et al. | |
| 2015/0230843 | A1 | 8/2015 | Palmer et al. | |
| 2019/0000451 | A1 | 1/2019 | Majors et al. | |
| 2019/0192160 | A1 | 6/2019 | Stamp | |
| 2020/0008807 | A1 | 1/2020 | Hollis | |
| 2022/0265270 | A1 * | 8/2022 | Stamp | A61B 17/0682 |
| 2023/0200809 | A1 * | 6/2023 | Wahl | A61B 17/064 606/101 |

FOREIGN PATENT DOCUMENTS

WO 2019231622 A1 12/2019

OTHER PUBLICATIONS

Extended European Search Report from corresponding Application No. 25155372.3, mailed Jun. 6, 2025, 5 pages.
UK Search and Examination Report from corresponding Application No. 2501446.5, mailed May 1, 2025, 4 pages.

* cited by examiner

*Primary Examiner* — Michelle Lopez
(74) *Attorney, Agent, or Firm* — Secant IP, P.L.L.C.

(57) ABSTRACT

The present disclosure provides bone/wound staple delivery devices. The staple delivery devices are configured to allow a user to prepare a staple for delivery into a patient, and also to hold the staple such that, even if the staple delivery device is no longer held by the operator, the staple will remain clamped and splayed for insertion into a bone.

20 Claims, 14 Drawing Sheets

FIG. 8
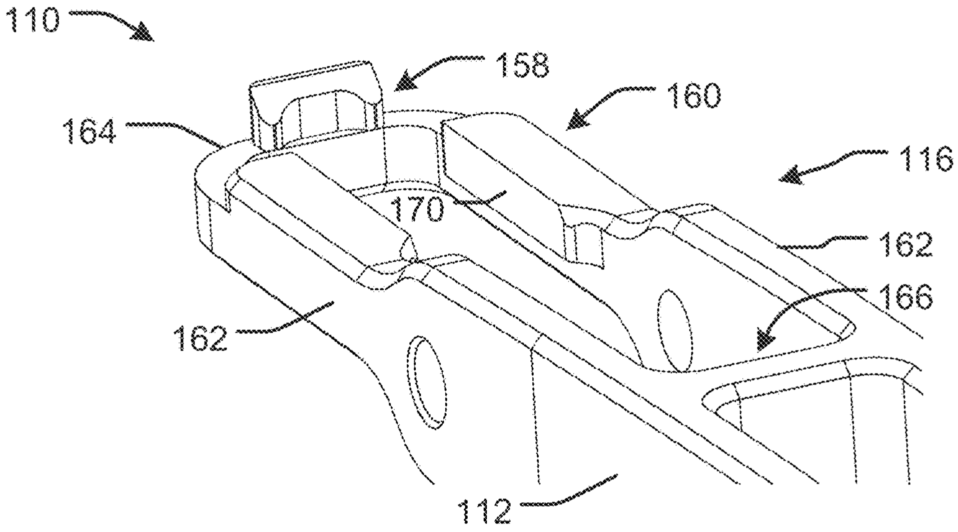
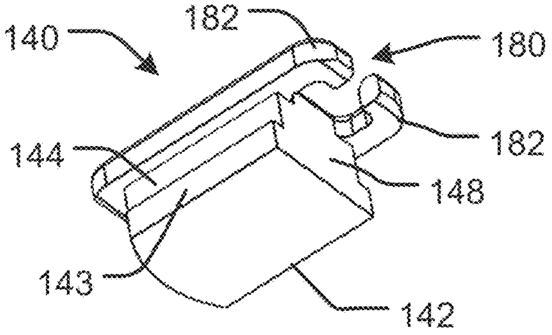
FIG. 9
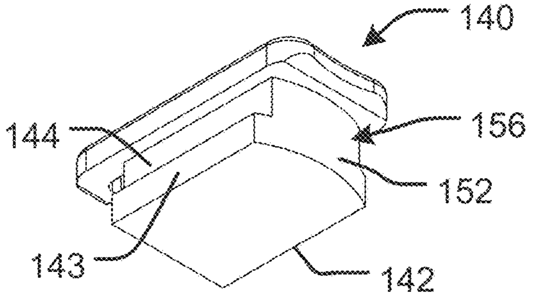
FIG. 10
FIG. 11
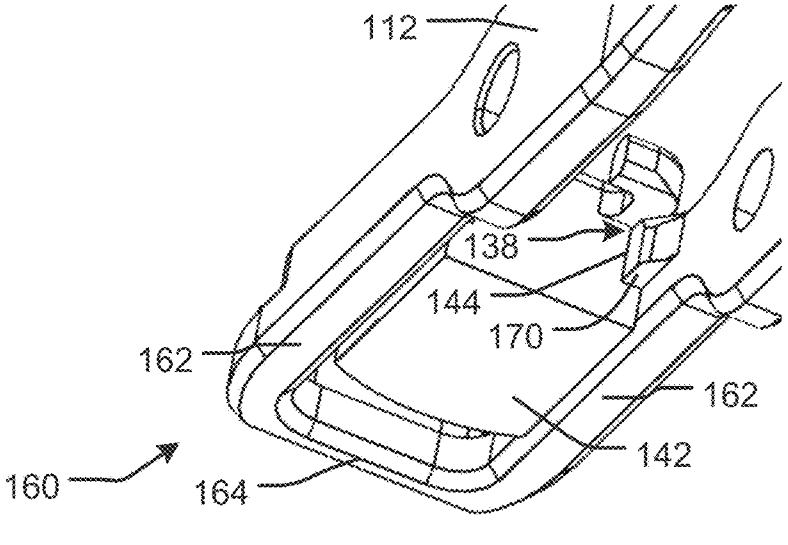
110 158 160 164 116 170 162 166 162 112
140 182 180 144 182 148 143 142
140 144 156 152 143 142

BONE STAPLE DELIVERY DEVICES, BONE STAPLES AND METHODS OF USE THEREOF

FIELD

The present disclosure relates to medical devices, particularly bone staple delivery devices, bone staples and methods of use thereof.

BACKGROUND

Bone staples are used to hold a fractured bone together, particularly by providing a compression force which urges the adjacent bone segments on each side of the fracture towards one another. The staple generally comprises a crown, with two legs at opposing ends of the crown. The staple is disposed in the bone, with the crown spanning the fracture and each of the legs residing in one of the adjacent bone segments.

Prior to being disposed in the bone segments, the staple is placed into a delivery device, which splays the legs away from one another with elastic deformation of the staple. When the staple is released from the delivery device, the elastic memory force of the staple causes the legs to elastically recover towards one another. The force associated with the staple legs being urged back towards one another due to elastic memory provides the compression force which urges the adjacent bone segments on each side of the fracture towards one another.

SUMMARY

The present disclosure provides a medical device, comprising a bone staple delivery device. The bone staple delivery device comprises an elongated platform and a lever-actuator. The platform and the lever-actuator form a staple clamp to clamp a bone staple. The lever-actuator has a lever-handle and a lever-head, with the lever-handle rotatable relative to the platform and having a distal end face comprising a planar distal end face and an arcuate distal end face. The lever-head has a planar proximal end face.

When the staple is installed in the clamp staple and the lever-handle is rotated with a closure force in a first direction towards to the platform, the bone staple delivery device is operable such that the arcuate distal end face of the lever-handle contacts the planar proximal end face of the lever-head and moves the lever-head distally relative to the platform to close the staple clamp on the staple.

When the lever-handle is further rotated with the closure force in the first direction towards to the platform, the planar distal end face of the lever-handle and the planar proximal end face of the lever-head come into parallel alignment facing one another, which inhibits the lever-handle from rotating in a second direction away from the platform upon removal of the closure force.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIG. 8 is a closed-up perspective view of a distal region of a platform of the bone stable delivery device of FIG. 1;

FIG. 9 is a perspective view of a lever-head of the bone stable delivery device of FIG. 1;

FIG. 10 is another perspective of a lever-head of the bone stable delivery device of FIG. 1;

FIG. 11 is a perspective view of the lever-head and the distal region of the platform of the bone stable delivery device of FIG. 1;

DETAILED DESCRIPTION

Figure 1:
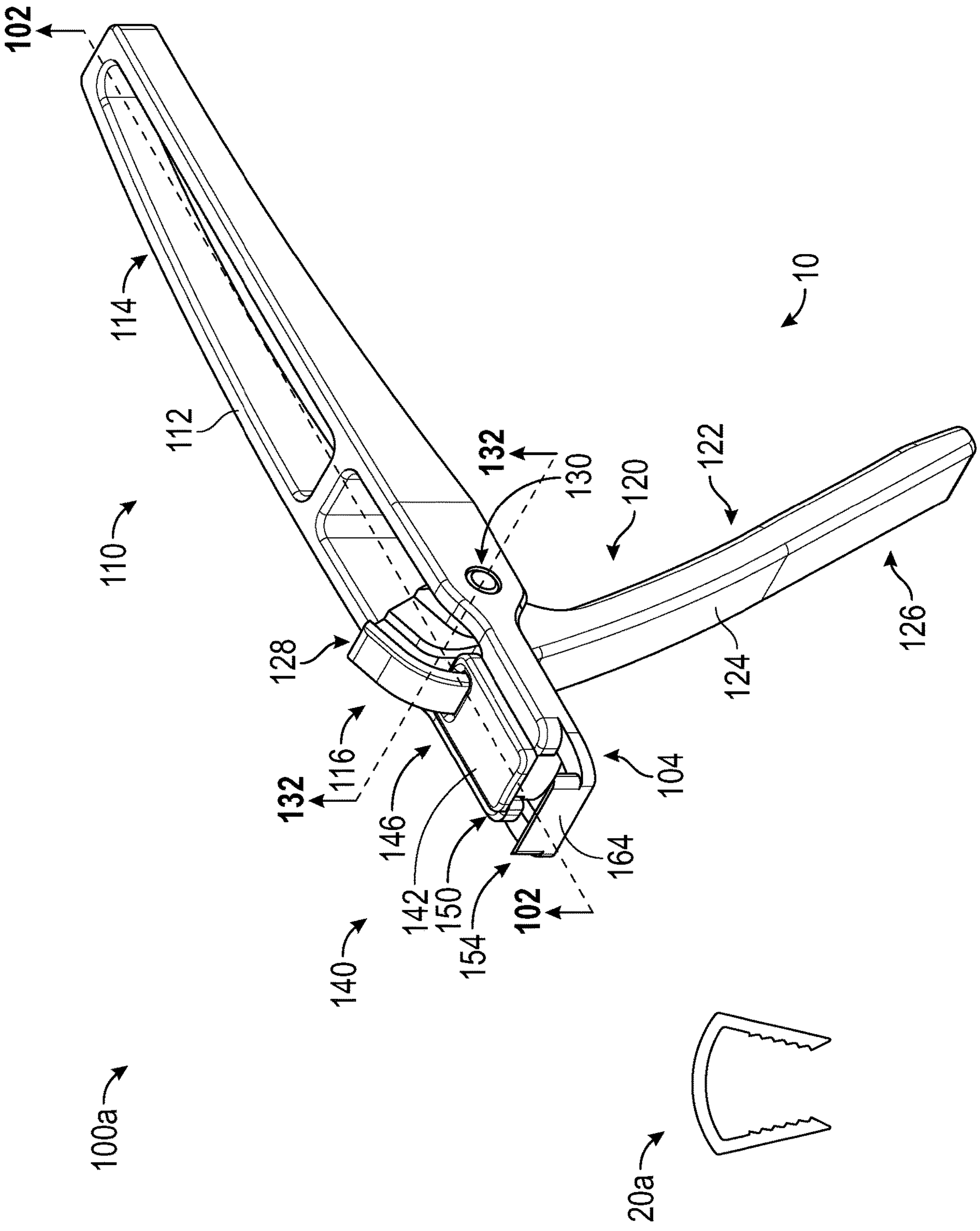
FIG. 1 is a perspective view of a medical device according to the present disclosure, comprising a bone staple delivery device and a staple.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Referring now to the figures, FIG. 1 shows a medical device 10 according to the present disclosure, comprising a manually (hand-operated) bone staple delivery device 100*a* and a bone staple 20*a*. Staple delivery device 100*a* is used to deliver the bone staple 20*a* to a host, particularly to facilitate repair of a bone fracture.

Figure 2A:
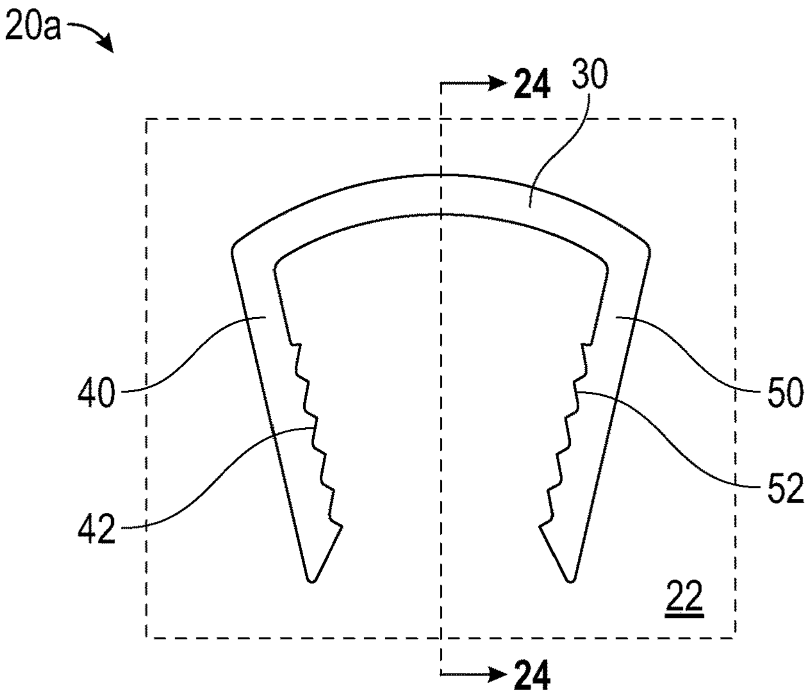
FIG. 2A is an enlarged side view of the staple of FIG. 1.

As best shown by FIG. 2A, bone staple 20*a* comprises an arcuate/bowed (convex) crown 30 (which may be understood to define the width of the staple) and two fastening legs 40, 50 disposed at the lateral ends of the crown 30. As shown, the crown 30 and the legs 40, 50 extend and are fully disposed in a frontal (common) plane 22, with the crown 30 being convex continually outwardly away from the legs 40, 50 as the crown 30 extends medially away from the legs 40, 50 towards a longitudinal midline 24 of the staple 20*a*/crown 30. Also as shown, the legs 40, 50 linearly and continually taper towards one another (converge) as the legs 40, 50 extend away from the crown 30, with the inner faces of each of the legs 40, 50 facing one another including a plurality of reverse barbs 42, 52 arranged along a longitudinal length of the legs 40, 50. Staple 20*a*, as well as staple 20*b* of FIG. 2*b*, may be formed of nitinol.

Returning to FIG. 1, staple delivery device 100*a* comprises an elongated platform 110 having a longitudinal length which extends along longitudinal axis 102 of the staple delivery device 100. As shown, elongated platform 110, which comprises an elongated platform body 112 (shown as a one-piece body), has a proximal (hand grasping end) region 114 and a distal (working end) region 116. As used herein, the terms "proximal" and "distal" may be understood as being relative to an operator (e.g. medical practitioner such as a doctor) of the staple delivery device 100*a*.

Staple delivery device 100*a* further comprises an elongated, lever-actuator 120, which both rotates/pivots relative to the platform 110, as well as moves translationally relative to the platform 110. More particularly, the lever-actuator 120 comprises a lever-handle 122 which rotates/pivots relative to the platform 110, and a lever-head 140 which moves translationally relative to the platform 110.

Lever-handle 122 has a longitudinal length which may extend along longitudinal axis 102 of the staple delivery device 100, depending on the rotational position of the lever-handle 122. Lever-handle 122 rotates about a pivot axis 132 of a pivot 130, shown provided by a pivot pin. Lever-handle 122, which comprises an elongated lever-handle body 124 (shown as a one-piece body), has a lever-handle proximal (hand grasping end) region 126 and a lever-handle distal (working end) region 128.

Translationally moveable lever-head 140 has a longitudinal length which extends along longitudinal axis 102 of the staple delivery device 100. Lever head 140 slides with linear movement along a longitudinal axis 102 of the staple delivery device 100*a*, which is also the longitudinal axis of the platform 110 and the lever-head 140. As shown, the longitudinal axis 102 and the pivot axis 132 are transverse, particularly perpendicular, to each other. Lever-head 140, which comprises a lever-head body 142 (shown as a one-piece body), also has a lever-head proximal region 146 and a lever-head distal region 150.

As shown, the lever-head 140, particularly the proximal region 146, is positively mechanically coupled (against separation) to the lever-handle 122, particularly the distal region 128. As explained in greater detail below, when the lever-handle 122 is rotated towards the elongated platform 110, and more particularly the proximal region 126 rotated towards the proximal region 114 of the platform 110, the lever-head 140 moves linearly distally along the longitudinal axis 102 of the staple delivery device 100*a*. Conversely, when the when the lever-handle 120 is rotated away from the elongated platform 110, and more particularly the proximal region 126 rotated away from the proximal region 114 of the platform 110, lever-head 140 moves linearly proximally along the longitudinal axis 102 of the staple delivery device 100*a*.

Figure 3:
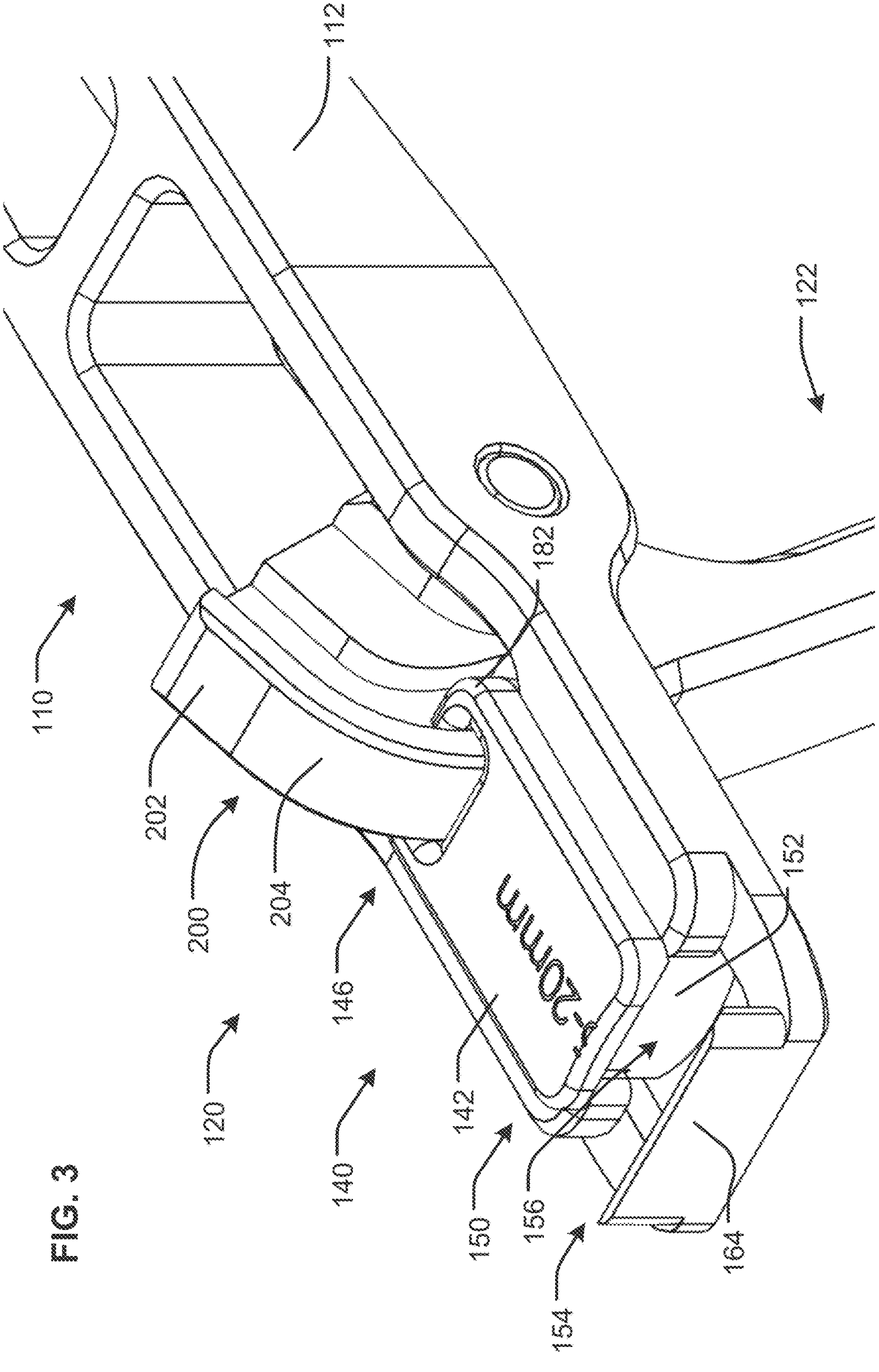
FIG. 3 is close-up perspective view of a distal region of the bone staple delivery device of FIG. 1.
Figure 4:
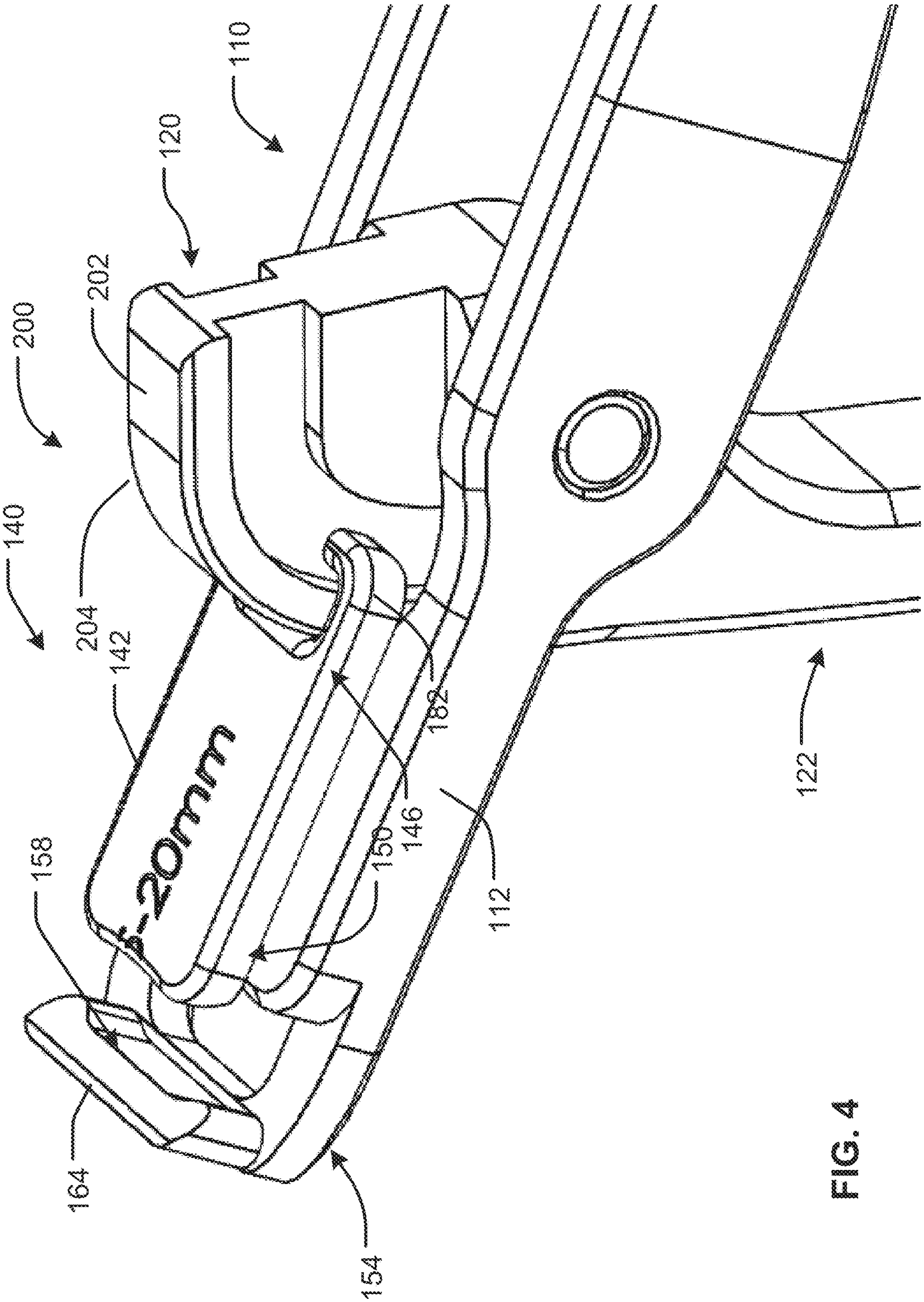
FIG. 4 is another close-up perspective view of the distal region of the bone staple delivery device of FIG. 1.

As shown in FIG. 1, the staple delivery device 100*a* includes staple clamp 154 at a working end 104 of the staple delivery device 100*a*. As better shown in FIG. 3, the staple clamp 154 comprises a opposing proximal clamp face 156 (formed by lever-head distal (end) face 152 of lever-head 140) and, as better shown in FIG. 4, distal clamp face 158 (formed by end wall 164 of the distal region 116 of platform 110).

Figure 5:
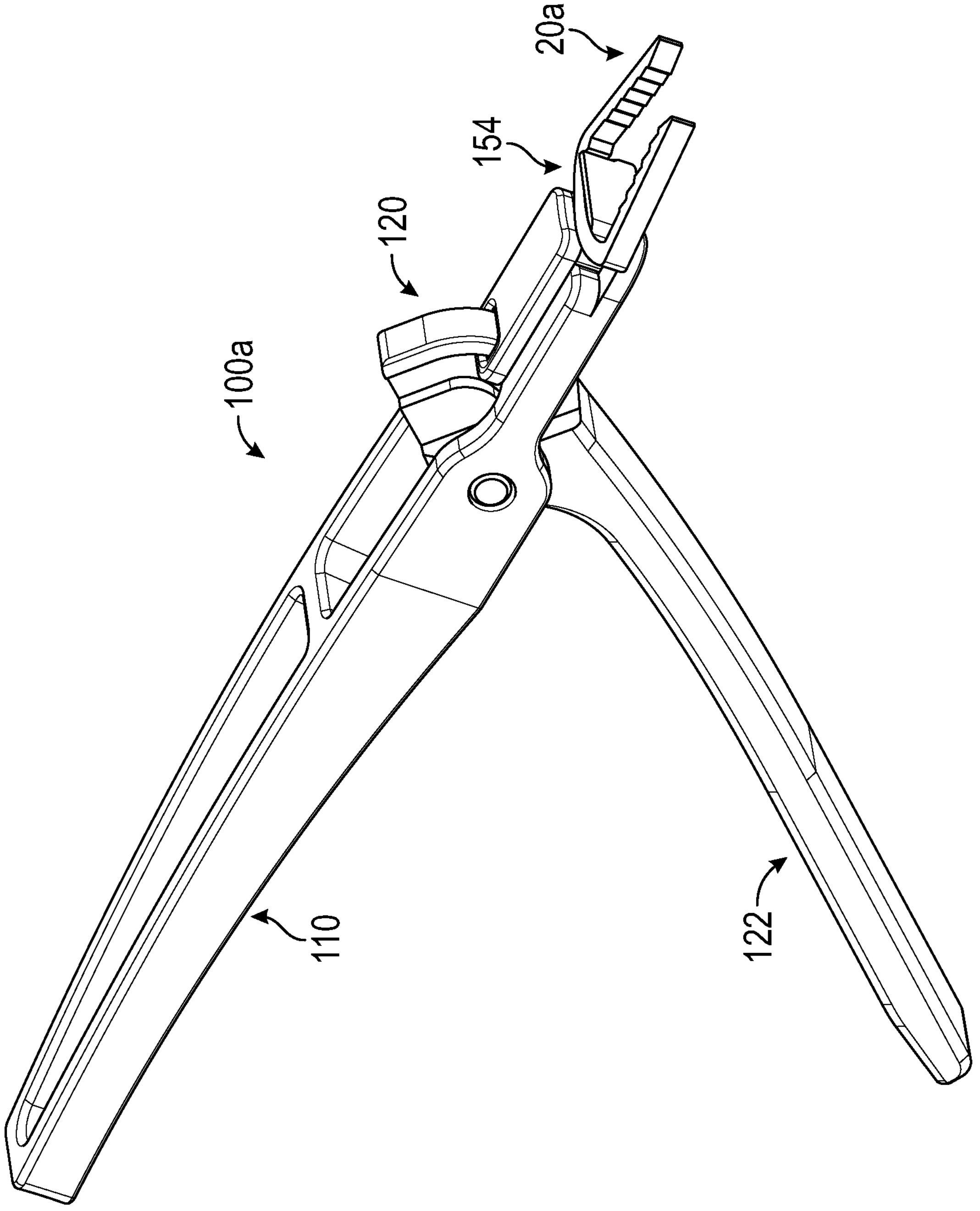
FIG. 5 is a perspective view of the medical device of FIG. 1, with the bone staple installed in the bone staple delivery device and the staple undeformed.
Figure 6:
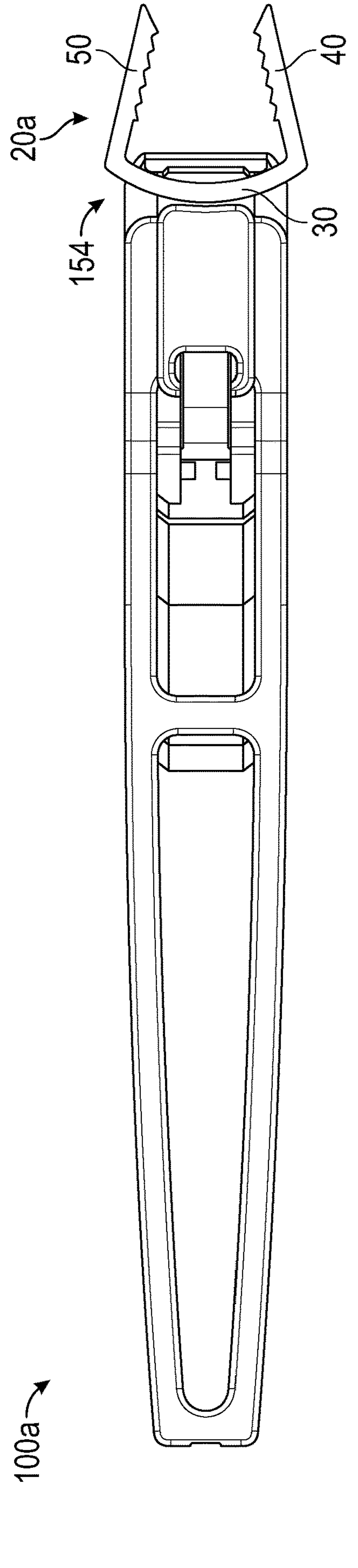
FIG. 6 is a top view of the medical device of FIG. 1, with the bone staple installed in the bone staple delivery device and the staple unclamped and undeformed.

Referring to FIG. 5, there is shown staple 20*a* installed in clamp 154, with clamp 154 in the staple installed position (which may also be referred to as clamp open position), in which the staple 20*a* is in an unclamped (or undeformed) state. Referring to FIG. 6, such is a top view of FIG. 5. As shown in FIGS. 5 and 6, the legs 40, 50 linearly and continually taper towards one another as the legs 40, 50 extend away from the crown 30.

Figure 7:
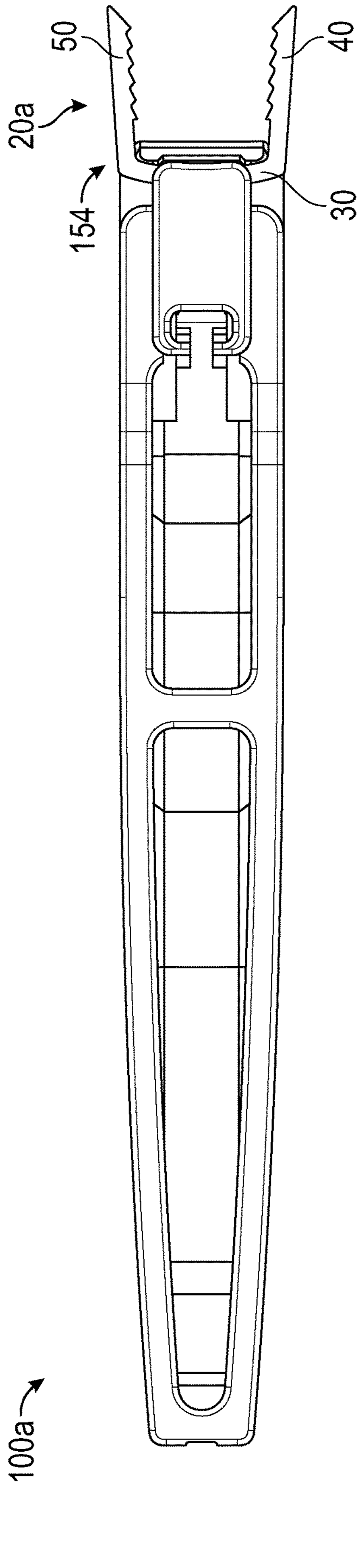
FIG. 7 is a top view of the medical device of FIG. 1, with the bone staple installed in the bone staple delivery device and the staple clamped and deformed.
Figure 12:
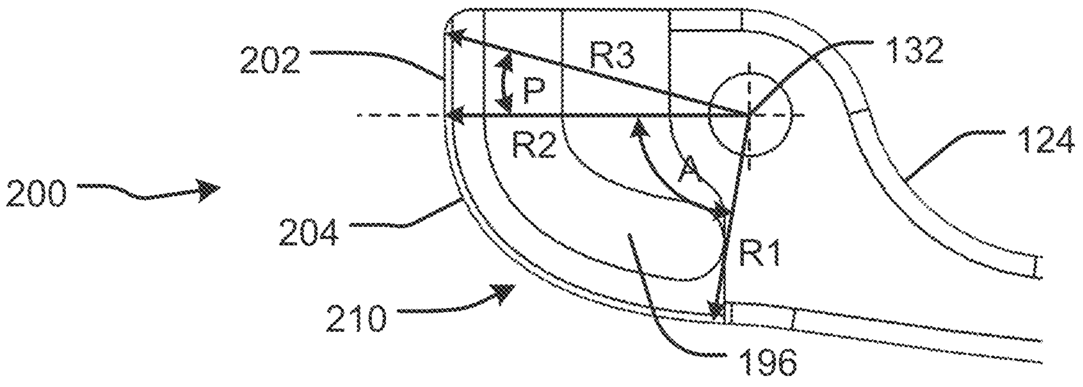
FIG. 12 is a side view of a distal region of a lever-handle of the bone stable delivery device of FIG. 1.
Figure 13:
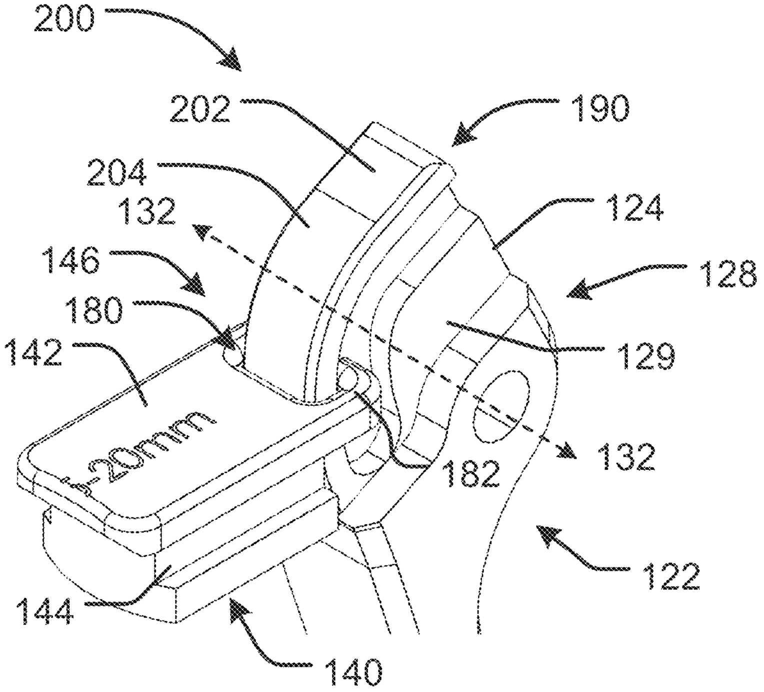
FIG. 13 is a perspective view of a distal region of the lever-handle and the lever-head of the bone stable delivery device of FIG. 1.
Figure 14:
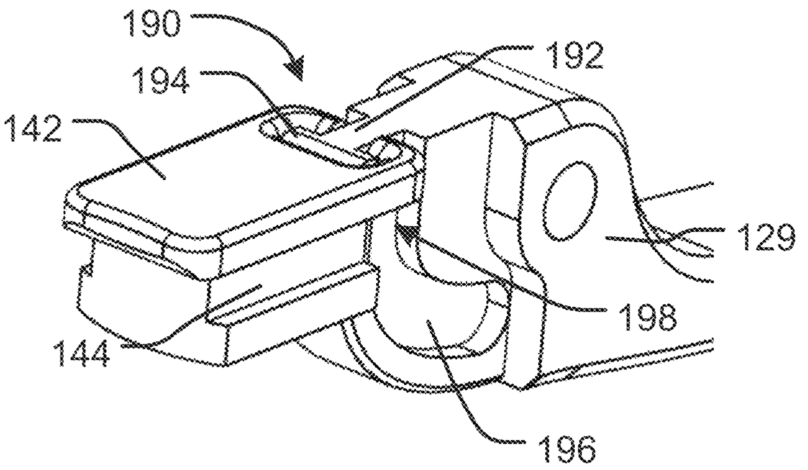
FIG. 14 is another perspective view of the distal region of the lever-handle and the lever-head of the bone stable delivery device of FIG. 1.
Figure 15:
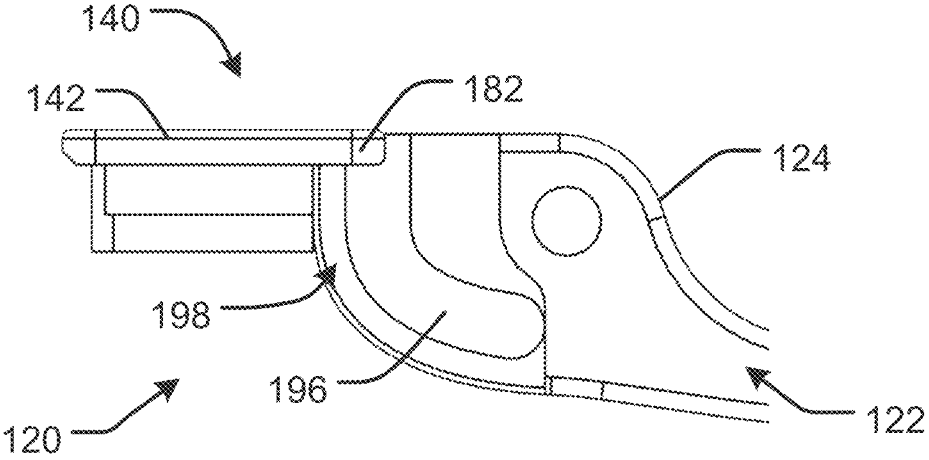
FIG. 15 is a side view of the distal region of the lever-handle and the lever-head of the bone stable delivery device of FIG. 1.
Figure 16:
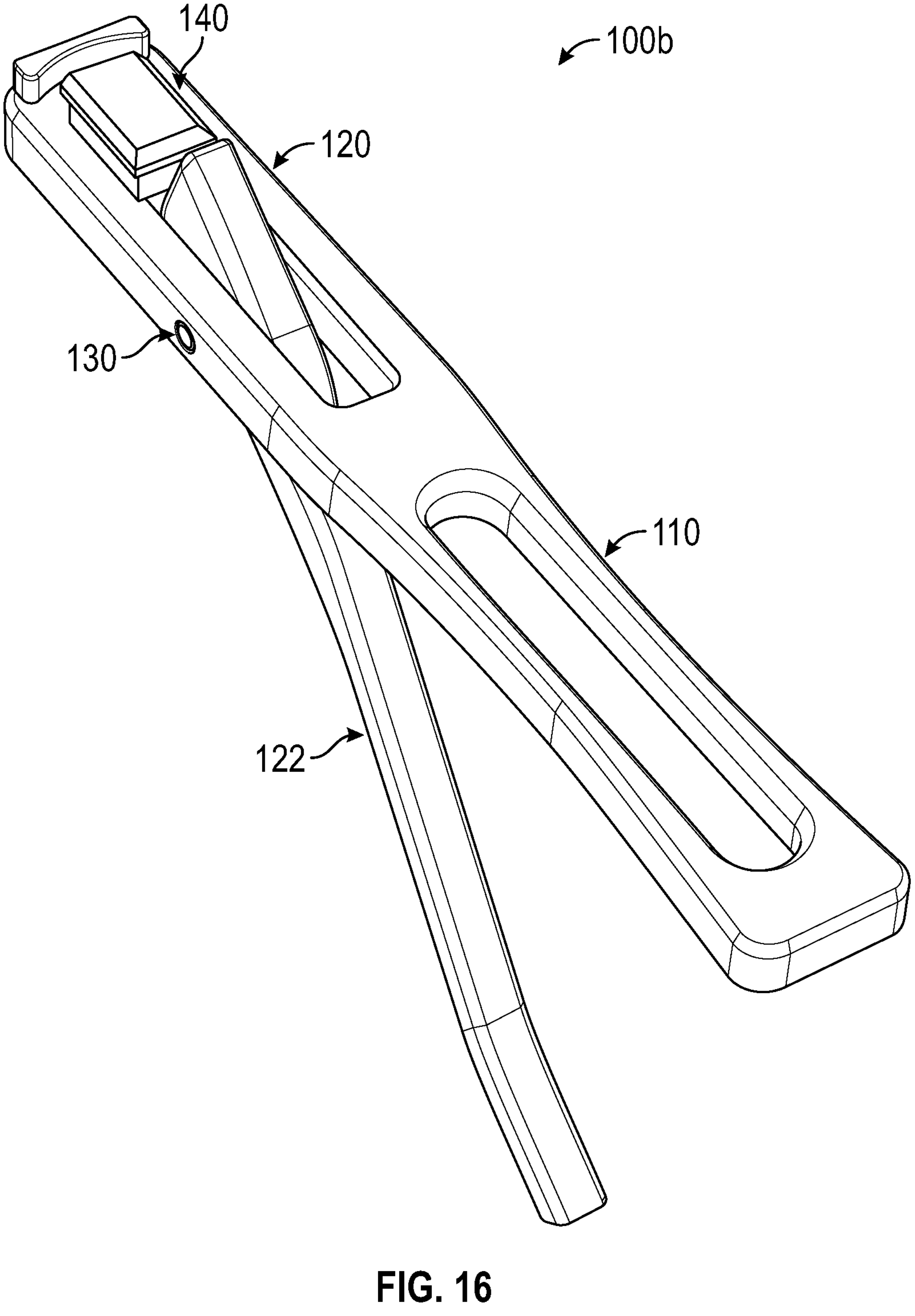
FIG. 16 is a perspective view of another bone staple delivery device according to the present disclosure.
Figure 17:
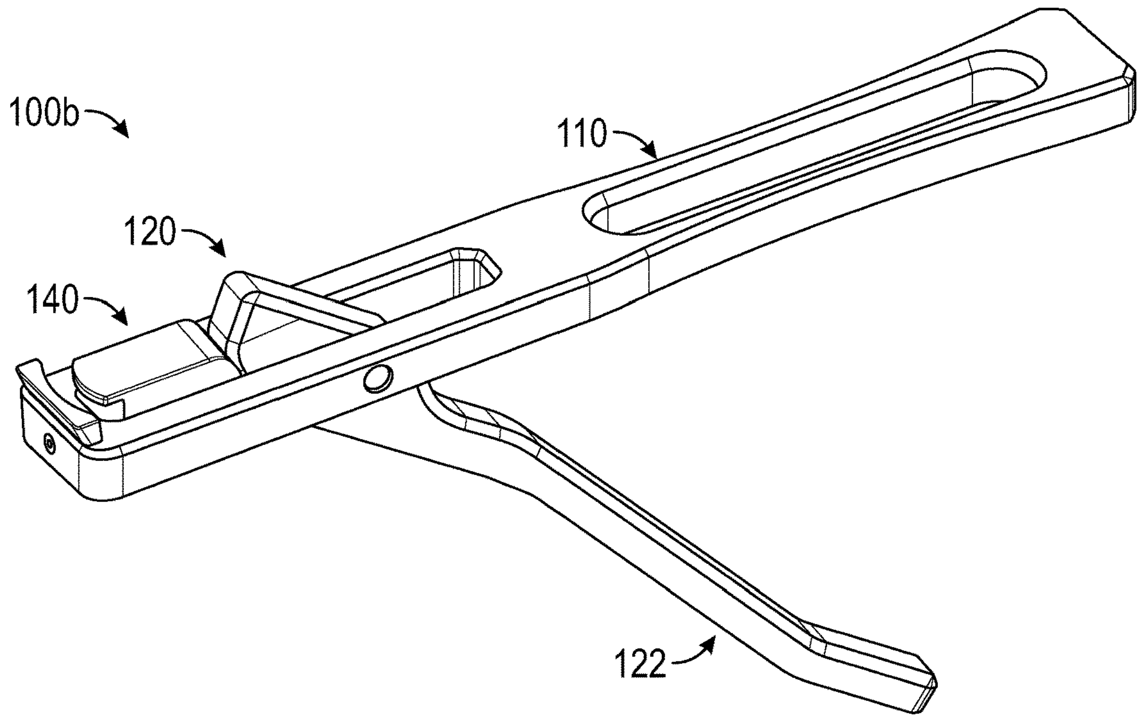
FIG. 17 is another perspective view of the bone staple delivery device of FIG. 16.
Figure 18:
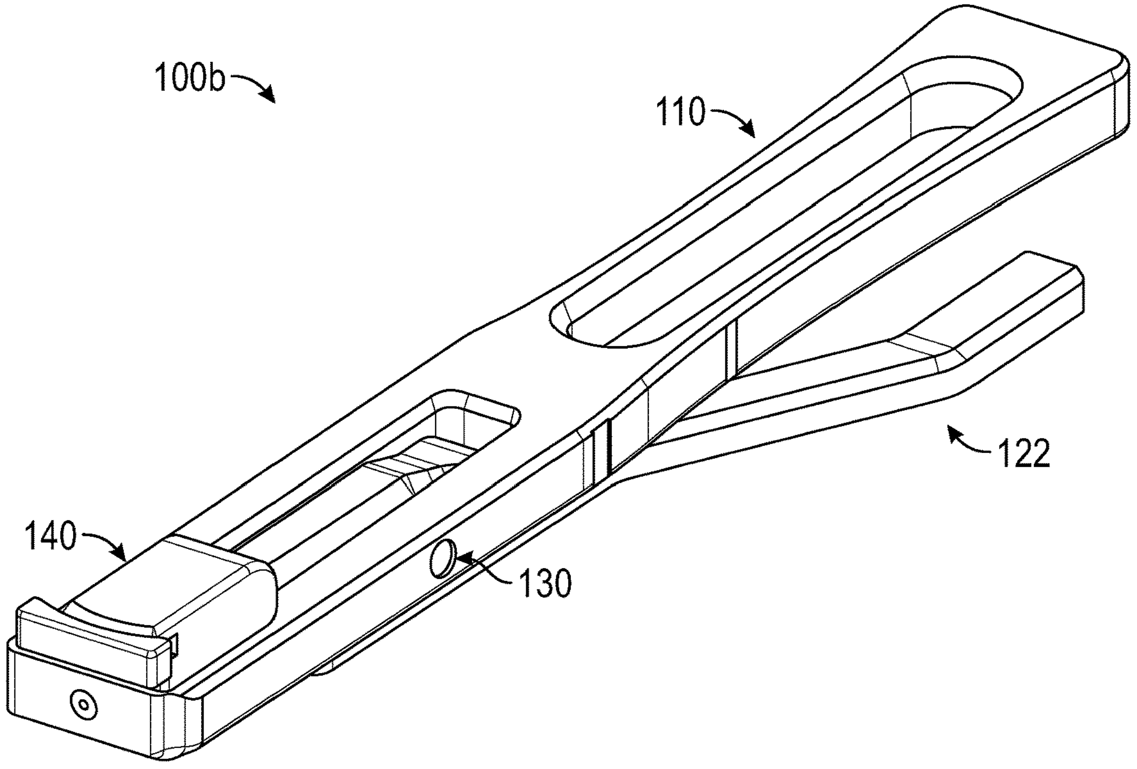
FIG. 18 is another perspective view of the bone staple delivery device of FIG. 16.
Figure 19:
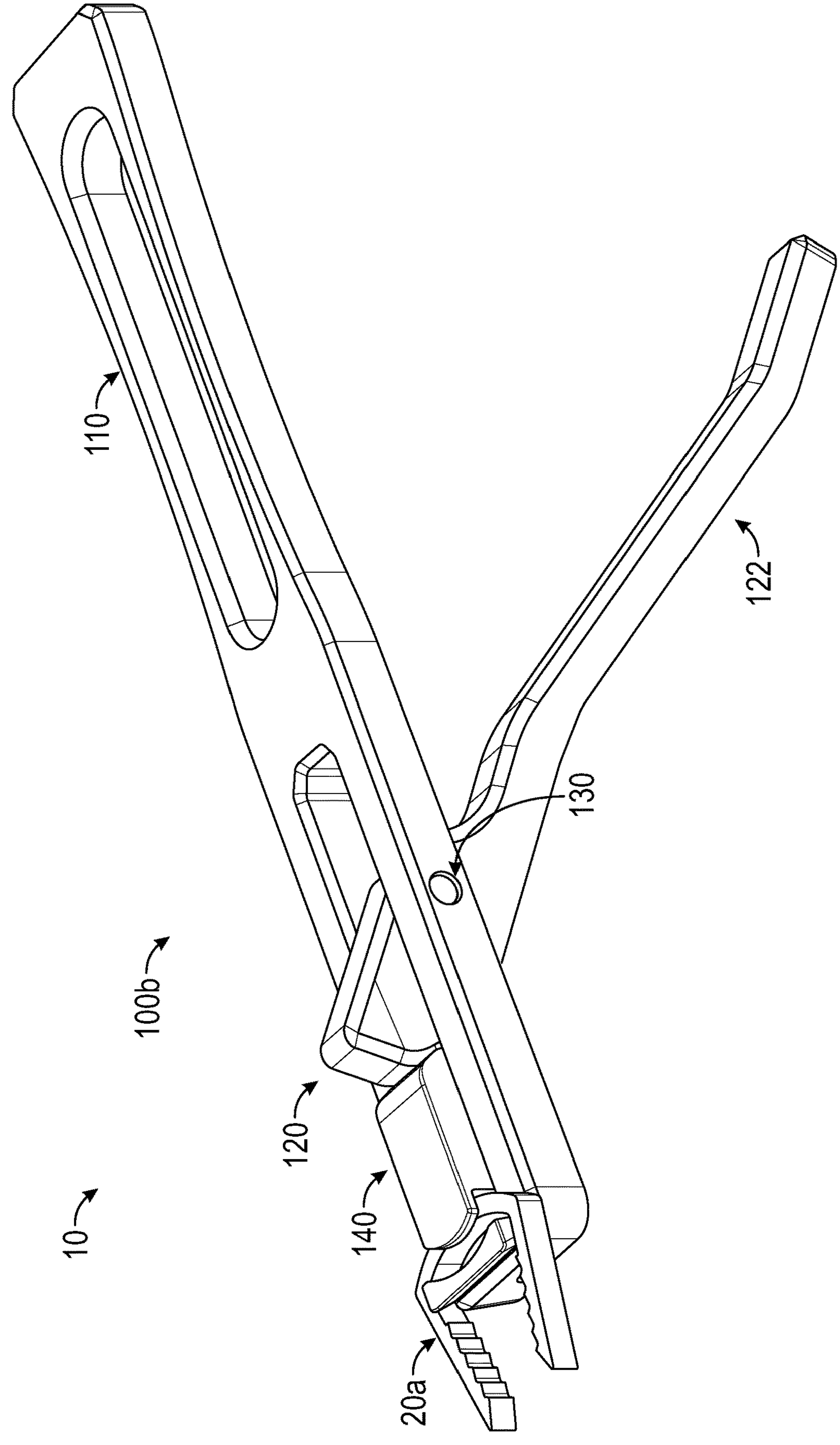
FIG. 19 is a perspective view of the bone staple installed in the bone staple delivery device of FIG. 16 and the staple unclamped and undeformed.
Figure 20:
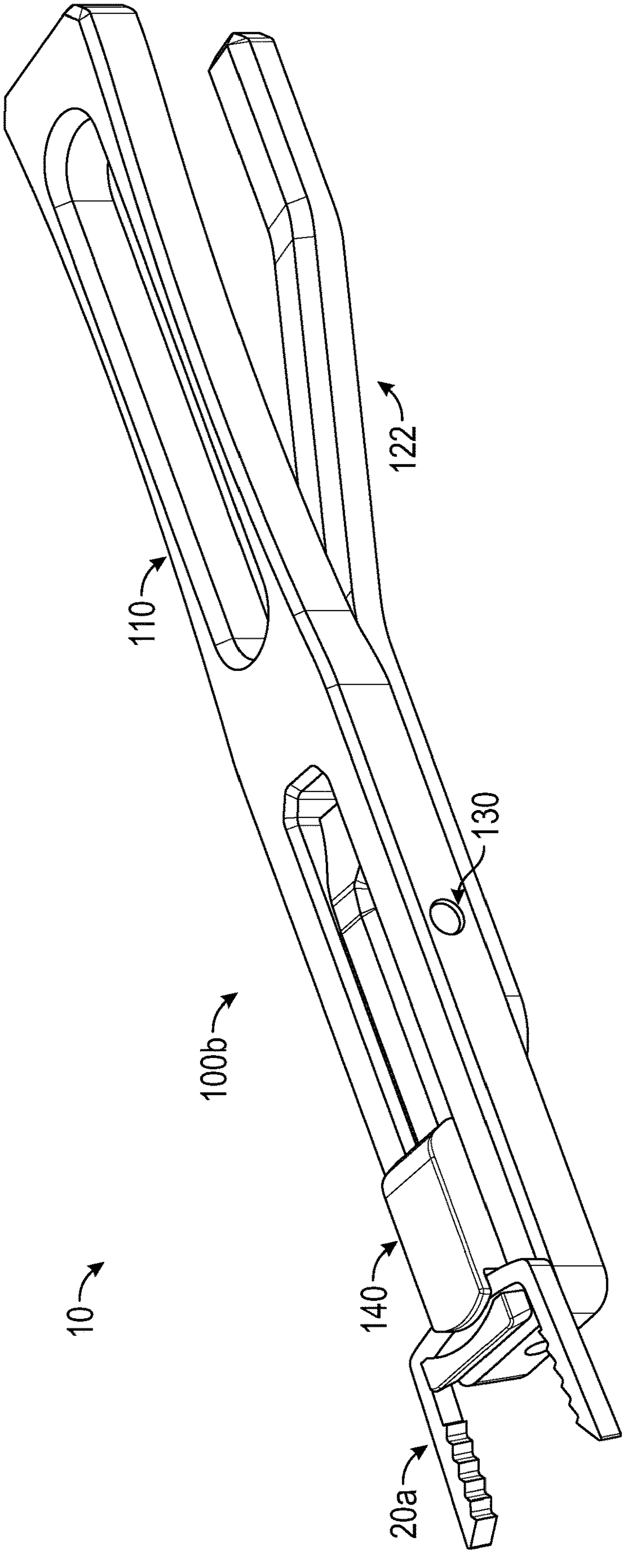
FIG. 20 is a perspective view of the bone staple installed in the bone staple delivery device of FIG. 16 and the staple clamped and deformed.

Now, referring to FIG. 7, clamp 154 in in a staple installed and clamped position (which may be referred to as the clamp closed position), in which the staple 20*a* is in a clamped (or elastically deformed) state. As shown, the crown 30 of the staple 20*a* in elastically deformed to flatten the arc/curvature of the crown 30, which, in turn, causes the legs 40, 50 of the staple 20*a* to splay (spread in the frontal plane 22 away from the midline 24) further apart and separate (diverge) as to become more parallel, particularly substantially parallel (e.g. within 10 degrees of being parallel). With the staple 20*a* arranged in this position, the staple 20*a* may be then disposed in a bone, with the crown 30 spanning the fracture and each of the legs 40, 50 residing in one of the adjacent bone segments. When the staple 20*a* is released from the staple delivery device 100*a*, the elastic memory of the staple 20*a*, and more particularly the crown 30, being urged towards its initial "bowed" state, causes the legs 40, 50 to attempt to elastically recover towards one another. The force associated with the staple legs 40, 50 being urged back towards one another due to clastic memory/recovery provides a compression force which urges the adjacent bone segments on each side of the fracture towards one another.

Referring now to FIGS. 8-11, the distal region 116 of the platform 110 is shown in FIG. 8, the lever-head 140 is shown in FIGS. 9-10 and the lever-head 140 assembled with the platform is shown in FIG. 11.

As shown by FIG. 8, the distal region 116 of the platform 110 comprises a U-shaped structure 160 having two longitudinally extending parallel arms 162 and a transverse distal end wall 164, which define a receiving space 166. As shown, arms 162 are mirror images of one another. The inner face of each arm 162 of the platform 110 includes a longitudinally extending protruding elongated linear rail 170, which is received in an elongated linear rail groove 144 of the lever-head 140, respectively formed on opposite lateral faces 143 of the lever-head 140. Such is shown in FIG. 11. In this manner, the linear rail 170 (which may be understood as a first connector) and the linear groove 144 (which may be understood a second mating connector which mates with the first connector) are positively mechanically coupled (against separation), particularly slidably engaged with a sliding linkage, relative to one another, and form a linear guide track 138 for proximal/distal movement of the lever-head 140.

Referring now to FIGS. 12-15, the proximal region 146 of the lever-head 140 and the distal region 128 of the lever-handle 122 are mechanically coupled such that rotational motion of the lever-handle 122 about pivot axis 132 in a first direction (e.g. away from proximal end region 114 of platform 110) causes linear (translational) motion of the lever-head 140 in a first direction (e.g. proximally), and rotational motion of the lever-handle 122 about pivot axis 132 in a second direction opposite the first direction (e.g. towards proximal end region 114 of platform 110) causes linear (translational) motion of the lever-head 140 in a second direction opposite the first direction (e.g. distally).

As shown, the proximal region 146 of the lever-head 140 comprises a T-shaped slot 180, which is formed by the proximal (end) face 148 of the lever-head 140 and two opposing, laterally spaced, curved, proximal end projections 182, which are more particularly shown as limbs having an elbow-shape, particularly L-shaped, with a 90° bend. As shown, projections 182 are mirror images of one another and, as the projections 182 extend proximally, the projections 182 curve towards one another and towards the longitudinal axis 102. As shown, the T-shaped slot 180 provides a receptacle to receive a T-shaped section 190 of the lever-handle 122. As shown, the T-shaped section 190 comprises a stem 192, which extends parallel with the longitudinal axis 102, and a crossbar 194, which extends transverse (perpendicular) to the stem 192 and the longitudinal axis 102. As shown, the opposite lateral faces 129 of the distal region 128 of the lever-handle 122 each include an arcuate groove 196, the bottom of which is defined by the stem 192. As shown, each curved projection 182 of the lever-head 140 is received in a one of the arcuate grooves 196 of the lever-handle 122, respectively. In this manner, the T-shaped section 190 of the lever-handle 122 (which may be understood as a first connector) and the T-shaped slot 180 of the lever-head 140 (which may be understood a second mating connector which mates with the first connector) are positively mechanically coupled (against separation), particularly slidably engaged with a sliding linkage, relative to one another. Further, an arcuate guide track 198 is formed by the projections 182 of the lever-head 140 being disposed in the grooves 196 of the lever-handle 122.

During operation, the proximal end face 148 of the lever-head 140 and the distal end face 200 of the lever-handle 122, operatively interact (contact) with one another. As shown, the proximal end face 148 of the lever-head 140 is planar (flat). As further shown, the distal end face 200 of the lever-handle 122 comprises a planar end face 202 and an arcuate end face 204 adjacent one another, which both extend a distance about (around) the pivot axis 132.

Arcuate end face 204 is a cam surface, of a cam 210 which has a continually increasing radial distance to the pivot axis 132 from radial distance R1 to radial distance R2. As shown, the increasing radial distance extends over subtended angle A of the arcuate end face 204, having the pivot axis 132 as the vertex. Stated another way, angle A is the angle subtended by the arcuate end face 204 from the vertex/pivot axis 132. As shown, the arcuate end face subtended angle A is an acute angle in a range of 75-85 degrees about the pivot axis 132. With regards to the planar end face 202, such extends from radial distance R2 to radial distance R3 over subtended angle P of the planar end face 202, also having the pivot axis 132 as the vertex. Stated another way, angle P is the angle subtended by the planar end face 202 from the vertex/pivot axis 132. As shown, the planar end face subtended angle P is an acute angle in a range of 20-30 degrees about the pivot axis 132.

As a result of the increasing radial distance over angle A as the proximal region 126 of the lever-handle 122 is rotated with a closure force towards the proximal region 114 of the platform 110, the arcuate end face 204 of the working region 128 of the lever-handle 122 contacts with and pushes against the planar proximal end face 148 of the lever-head 140, which force moves the lever-head 140 linearly distally along the longitudinal axis 102 of the staple delivery device **100*a*. During the rotation, the lever head 140 moves along the linear guide track 138 formed by the lever-head 140 and the platform 110, and also moves along the arcuate guide track 198 formed by the lever-head 140 and the lever-handle 122**.

As the lever-head 140 moves distally, the clamp 154, having proximal clamp face 156 formed by lever-head distal face 152 of lever-head 140) and distal clamp face 158 formed by end wall 164 of the distal region 116 of platform 110), closes and clamps crown 30 of staple **20*a*. As the clamp 154 closes and clamps crown 30 of staple 20*a*, the crown 30 of the staple 20*a* in elastically deformed to flatten the arc/curvature of the crown 30, which, in turn, causes the legs 40, 50 of the staple 20*a* to splay (spread in the frontal plane 22 away from the midline 24**) further apart and separate (diverge) as to become more parallel.

It should be noted that, as the lever-handle 122 is rotated towards the elongated platform 110, and the arcuate end face 204 of the working region 128 of the lever handle 122 pushes against the planar proximal end face 148 of the lever-head 140, a bias force is applied to the lever-handle 122 by the elastically deformed staple **20*a* which urges the lever-handle 122 to rotate in the opposite direction. Thus, if the manual (hand-applied) force to clamp the staple 20*a* is removed while the arcuate end face 204 of the working region 128 of the lever handle 122 is acting on the planar proximal end face 148 of the lever-head 140 (e.g. the staple delivery device 100*a* is no longer held by the operator), the lever-handle 122 will rotate away from the platform 110 and the clamping force on the staple 20*a*** will be lost.

However, as the lever-handle 122 is further rotated towards the elongated platform 110, the planar end face 202 of the working region 128 of the lever handle 122 aligns with the planar proximal end face 148 of the lever-head 140 subsequent to the arcuate end face 204, such that the end faces 148, 202 face one another and become parallel, with the resilient (bias) force of the staple **20*a* forcing the planar end face 148 of the lever-head 140 towards and into contact with the planar end face 202 of the lever-handle 122**.

In the foregoing manner, once the arcuate end face 204 of the lever-handle 140 is no longer in contact with the planar proximal end face 148 of the lever-head 140, the lever-actuator 120 is now held and maintained stationary against the resilient (bias) force of the staple **20*a* acting on the level actuator 120. Thus, in this state, even if the staple delivery device 100*a* is no longer held by the operator, the staple 20*a* will remain clamped with the legs 40, 50** splayed for insertion into a bone.

When the legs 40, 50 are splayed and inserted into a bone, the lever-handle 22 may then be rotated in the opposite direction, i.e. away from the elongated platform 110, to open the clamp 154 and release the staple **20*a*. As the lever-handle 122 is rotate away from the elongated platform 110, the projections 182 of the lever-head 140 move within the grooves 196 of the lever-handle 122, and the T-shaped section 190 of the lever-handle 122 pulls the lever-head 140** proximally.

Turning to the embodiment of FIGS. 16-20, with staple delivery device **100*b*, the lever-head 140 is no longer mechanically coupled to the lever-handle 122. Similar to the prior embodiment, when the proximal region 126 of the lever-handle 122 rotated towards the proximal region 114 of the platform 110, the lever-head 140 moves linearly distally along the longitudinal axis 102 of the staple delivery device 100***b*. However, when the proximal region 126 of the lever-handle 122 rotated away from the proximal region 114 of the platform 110, lever-head 140 will not move linearly proximally along the longitudinal axis 102 of the staple delivery device 100*b* due to the absence of the mechanical coupling of the lever-head 140 and the lever-handle 112. Rather, lever-head 140 must be moved manually (by hand).

Figure 2B:
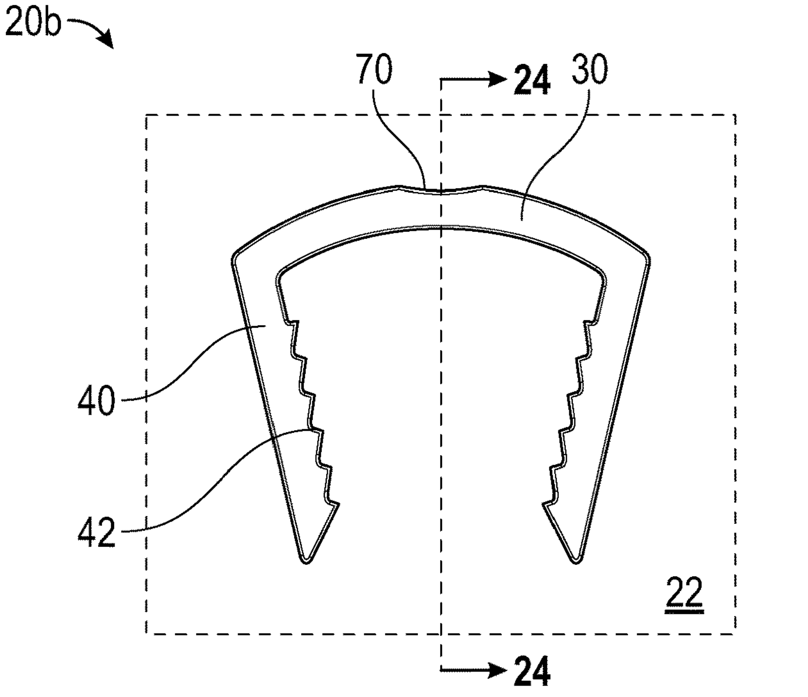
FIG. 2B is an enlarged side view of another staple according to the present disclosure.
Figure 21:
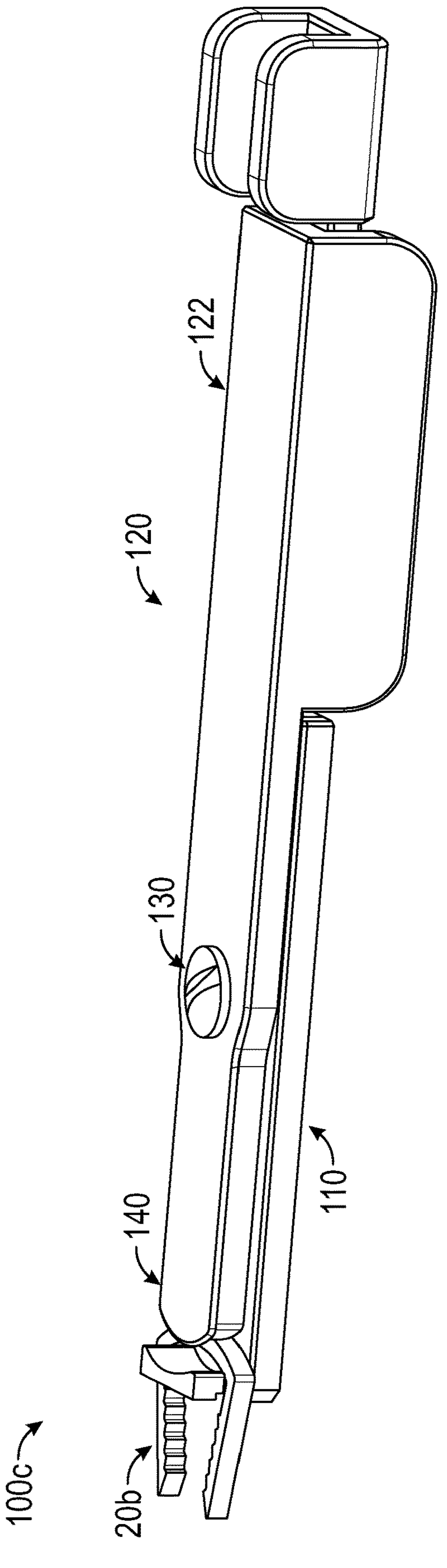
FIG. 21 is a perspective view of another bone staple delivery device and the staple of according to the present disclosure.

Turning to the embodiment of FIG. 21, such makes use of staple 20*b* of FIG. 2B, which includes a crown detent 70 to receive the lever-head 140 which is now formed as one-piece with the lever-handle 122. Also as shown, the lever-handle 122 rotates parallel to the platform 110, about pivot screw 130. Thus, the embodiment of FIG. 21 operates in a "scissor-like" manner to rotate the lever handle 122 relative to the platform 110.

While a preferred embodiment of the present invention(s) has been described, it should be understood that various changes, adaptations and modifications can be made therein without departing from the spirit of the invention(s) and the scope of the appended claims. The scope of the invention(s) should, therefore, be determined not with reference to the above description, but instead should be determined with reference to the appended claims along with their full scope of equivalents. Furthermore, it should be understood that the appended claims do not necessarily comprise the broadest scope of the invention(s) which the applicant is entitled to claim, or the only manner(s) in which the invention(s) may be claimed, or that all recited features are necessary.

LISTING OF REFERENCE CHARACTERS

10 medical device
20 bone staple (20*a*. 20*b*)
22 plane
24 midline
30 crown
40 leg
42 barb
50 leg
52 barb
70 detent
100 bone staple delivery device (100*a*, 100*b*, 100*c*)
102 longitudinal axis
104 working end
110 platform
112 platform body
114 platform proximal (grasping end) region
116 platform distal (working end) region
120 lever-actuator
122 lever-handle
124 lever-handle body
126 lever-handle proximal (grasping end) region
128 lever-handle distal (working end) region
129 lever-handle lateral face
130 pivot
132 pivot axis
138 guide track
140 lever-head
142 lever-head body
143 lever-head lateral face
144 lever-head groove
146 lever-head proximal region
148 lever-head proximal (end) face
150 lever-head distal (end) region
152 lever-head distal (end) face
154 clamp
156 proximal clamp face
158 distal clamp face
160 platform body U-shaped structure
162 platform arms
164 platform transverse end wall
166 platform receiving space
170 platform rail
180 lever-head T-shaped slot
182 lever-head projections
190 lever-handle T-shaped section
192 stem
194 crossbar
196 groove
198 arcuate guide track
200 lever-handle distal end face
202 planar end face
204 arcuate end face
210 cam
A arcuate end face subtended angle
P planar end face subtended angle
R1 radial distance 1
R2 radial distance 2
R3 radial distance 3.

What is claimed is:

1. A medical device, comprising:

a bone staple delivery device, the bone staple delivery device comprising an elongated platform and a lever-actuator;

the platform and the lever-actuator forming a staple clamp to clamp a bone staple;

the lever-actuator having a lever-handle and a lever-head, the lever-handle rotatable relative to the platform and having a distal end face comprising a planar distal end face and an arcuate distal end face;

the lever-head having a planar proximal end face;

wherein, when the staple is installed in the staple clamp and the lever-handle is rotated with a closure force in a first direction towards to the platform, the bone staple delivery device is operable such that the arcuate distal end face of the lever-handle contacts the planar proximal end face of the lever-head and moves the lever-head distally relative to the platform to close the staple clamp on the staple; and wherein, when the lever-handle is further rotated with the closure force in the first direction towards to the platform, the planar distal end face of the lever-handle and the planar proximal end face of the lever-head come into parallel alignment facing one another, which inhibits the lever-handle from rotating in a second direction away from the platform upon removal of the closure force.

2. The medical device of claim 1, wherein:

the lever-handle is rotatable relative to the platform about a pivot axis:

the arcuate distal end face of the lever-handle extends around the pivot axis with an increasing radial distance from the pivot axis.

3. The medical device of claim 1, wherein:

the planar distal end face of the lever-handle is adjacent the arcuate distal end face of the lever-handle.

4. The medical device of claim 2, wherein:

an angle subtended by the arcuate distal end face of the lever-handle from the pivot axis is in a range of 75-85 degrees.

5. The medical device of claim 2, wherein:
an angle subtended by the planar distal end face of the lever-handle from the pivot axis is in a range of 20-30 degrees.

6. The medical device of claim 1, wherein:
the bone staple delivery device has a longitudinal axis:
the platform extends along the longitudinal axis, and comprises a platform distal region;
the platform distal region comprises two longitudinally extending arms spaced apart by a receiving space which contains the lever-head.

7. The medical device of claim 6, wherein:
the lever-head and the platform distal region form at least one linear guide track along which the lever-head is movable proximally and distally along the longitudinal axis of the bone staple delivery device.

8. The medical device of claim 7, wherein:
the at least one linear guide track comprises a linear rail disposed in a linear groove.

9. The medical device of claim 8, wherein:
the platform distal end forms the linear rail; and
the lever-head forms the linear groove.

10. The medical device of claim 7, wherein:
the at least one linear guide track comprises two linear guide tracks along which the lever-head is movable proximally and distally along the longitudinal axis of the bone staple delivery device.

11. The medical device of claim 10, wherein:
each of the two linear guide tracks is formed by one of the longitudinally extending arms of the platform distal region and a lateral face of the lever-head, respectively.

12. The medical device of claim 11, wherein:
the lever-handle and the lever-head are mechanically coupled by a T-shaped section of the lever-handle disposed on a T-shaped slot of the lever-head.

13. The medical device of claim 6, wherein:
the lever-handle comprises a lever-handle distal region;
the receiving space contains the lever-handle distal region;
the lever-head and the lever-handle distal region form at least one arcuate guide track along which the lever-handle distal region is rotatable relative to the lever-head.

14. The medical device of claim 13, wherein:
the at least one arcuate guide track comprises a projection disposed in an arcuate groove.

15. The medical device of claim 14, wherein:
the lever-head forms the projection; and
the lever-handle distal region forms the arcuate groove.

16. The medical device of claim 13, wherein:
the at least one arcuate guide track comprises two arcuate guide tracks along which the lever-handle distal region is rotatable relative to the lever-head.

17. The medical device of claim 16, wherein:
each of the two arcuate guide tracks is formed by a projection of the lever-head and a lateral face of the lever-handle distal region, respectively.

18. The medical device of claim 1, wherein:
the platform comprises a platform proximal region;
the lever-handle comprises a lever-handle proximal region; and
each of the platform proximal region and the lever-handle proximal region comprise a hand-grasping region, respectively.

19. The medical device of claim 1, wherein:
the bone stable delivery device is a manually operable.

20. The medical device of claim 1, further comprising:
the bone staple installable in the bone staple delivery device.

* * * * *